United States Patent
Jansen et al.

(10) Patent No.: US 8,632,800 B2
(45) Date of Patent: Jan. 21, 2014

(54) MULTILAYER DRUG DELIVERY SYSTEM WITH BARRIER AGAINST RESERVOIR MATERIAL FLOW

(75) Inventors: Rolf R. Jansen, Redwood City, CA (US); Dina J. Coronado, Santa Clara, CA (US)

(73) Assignee: ALZA Corporation, Mountain View, CA (US)

( * ) Notice: Subject to any disclaimer, the term of this patent is extended or adjusted under 35 U.S.C. 154(b) by 2017 days.

(21) Appl. No.: 11/433,343

(22) Filed: May 12, 2006

(65) Prior Publication Data

US 2006/0257462 A1     Nov. 16, 2006

Related U.S. Application Data

(60) Provisional application No. 60/680,905, filed on May 13, 2005, provisional application No. 60/790,236, filed on Apr. 7, 2006.

(51) Int. Cl.
- *A61L 15/16* (2006.01)
- *A61F 13/02* (2006.01)
- *A61F 13/00* (2006.01)
- *A61K 9/70* (2006.01)

(52) U.S. Cl.
USPC .......................... 424/447; 424/448; 424/449

(58) Field of Classification Search
USPC ......................... 424/448, 447, 449
See application file for complete search history.

(56) References Cited

U.S. PATENT DOCUMENTS

| | | |
|---|---|---|
| 3,493,657 A | 2/1970 | Lewenstein et al. |
| 3,598,122 A | 8/1971 | Zaffaroni |
| 3,598,123 A | 8/1971 | Zaffaroni |
| 3,773,955 A | 11/1973 | Pachter et al. |
| 4,286,592 A | 9/1981 | Chandrasekaran |
| 4,314,557 A | 2/1982 | Chandrasekaran |
| 4,379,454 A | 4/1983 | Campbell et al. |
| 4,457,933 A | 7/1984 | Gordon et al. |
| 4,464,378 A | 8/1984 | Hussain |
| 4,568,343 A | 2/1986 | Leeper et al. |
| 4,588,580 A | 5/1986 | Gale et al. |
| 4,626,539 A | 12/1986 | Aungst et al. |
| 4,806,341 A | 2/1989 | Chien et al. |
| 4,849,224 A * | 7/1989 | Chang et al. .................. 424/434 |
| 4,935,428 A | 6/1990 | Lewis |
| 4,983,395 A * | 1/1991 | Chang et al. .................. 424/448 |
| 5,149,538 A | 9/1992 | Granger et al. |
| 5,236,714 A | 8/1993 | Lee et al. |
| 5,370,924 A | 12/1994 | Kochinke |
| 5,411,740 A | 5/1995 | Lee et al. |
| 5,693,335 A | 12/1997 | Xia et al. |
| 5,700,480 A | 12/1997 | Hille et al. |
| 5,785,991 A | 7/1998 | Burkoth et al. |
| 5,843,468 A | 12/1998 | Burkoth et al. |
| 5,877,172 A | 3/1999 | Hille et al. |
| 5,882,676 A | 3/1999 | Lee et al. |
| 5,932,238 A | 8/1999 | Opitz |
| 5,958,903 A | 9/1999 | Renko et al. |
| 6,004,578 A | 12/1999 | Lee et al. |
| 6,018,043 A | 1/2000 | Dyer et al. |
| 6,093,815 A | 7/2000 | Chaplin et al. |
| 6,184,004 B1 | 2/2001 | Bannister et al. |
| 6,194,404 B1 | 2/2001 | Hille et al. |
| 6,316,439 B1 | 11/2001 | Kosley, Jr. et al. |
| 6,323,195 B1 | 11/2001 | Kosley, Jr. et al. |
| 6,323,196 B1 | 11/2001 | Kosley, Jr. et al. |
| 6,335,328 B2 | 1/2002 | Hille et al. |
| 6,573,376 B2 | 6/2003 | Hille et al. |
| 6,617,452 B2 | 9/2003 | Hille et al. |
| 2003/0026829 A1 | 2/2003 | Venkatraman et al. |
| 2004/0013716 A1 * | 1/2004 | Gale et al. .................. 424/449 |
| 2004/0192683 A1 | 9/2004 | Moormann et al. |
| 2005/0065338 A1 | 3/2005 | Thal et al. |
| 2006/0257460 A1 | 11/2006 | Jansen et al. |
| 2006/0257461 A1 | 11/2006 | Jansen et al. |

FOREIGN PATENT DOCUMENTS

| | | |
|---|---|---|
| EP | 0449247 | 10/1991 |
| EP | 0680325 | 4/2002 |
| WO | WO-01/58451 | 8/2001 |
| WO | WO-02/087482 | 11/2002 |
| WO | WO-02/102803 | 12/2002 |
| WO | WO-03/090729 | 11/2003 |
| WO | WO 2005/018517 A1 | 3/2005 |

OTHER PUBLICATIONS

Satas, D. "Acrylic Adhesives", Handbook of Pressure-Sensitive Adhesive Technology 2nd Edition (1989); pp. 396-456.

Jansen, et al., "Multilayer Drug Delivery System With Barrier Against Antagonist Exposure," U.S. Appl. No. 11/432,871, filed May 12, 2006.

Jansen, et al., "Multilayer Galantamine Delivery System With Barrier Against Reservoir Material Flow," U.S. Appl. No. 11/432,918, filed May 12, 2006.

(Continued)

*Primary Examiner* — Richard Schnizer
*Assistant Examiner* — Katherine Peebles
(74) *Attorney, Agent, or Firm* — Stoel Rives LLP; Samuel E. Webb; Zhi-Xiang (Alex) Oh (57) ABSTRACT

A multilayered drug delivery system with a barrier suitable for delivery of drug through an individual's body surface. By placing a barrier between two adjacent layers, unintended drug flow due to migration of a drug matrix between the adjacent matrix layers in the system to a patient is avoided.

12 Claims, 6 Drawing Sheets

(56) References Cited

OTHER PUBLICATIONS

Levine, J.D., et al., "Potentiation of Pentazocine Analgesia by Low-Dose Naloxone," Journal of Clinical Investigations 82, pp. 1574-1577, (1988).

Crain, S.M., et al., "Antagonists of excitatory opioid receptor functions enhance morphine's analgestic potency and attenuate opioid tolerance/dependence liability," Pain 84, pp. 121-131, (2000).

Tan, et al., "Pressure-sensitive adhesives for transdermal drug delivery systems," Elsevier Science 1999, PSTT vol. 2, No. 2, (Feb. 1999).

Mann, et al., "Galantamine: a cholinergic patch in the treatment of alcoholism: a randomized, placebo-controlled controlled trial," Psychopharmacology, pp. 115-121, (2005).

International Search Report dated Mar. 12, 2007 in corresponding International Application No. PCT/US2006/018427.

International Search Report dated Mar. 7, 2007 in corresponding International Application No. PCT/US2006/018683.

* cited by examiner

MULTILAYER DRUG DELIVERY SYSTEM WITH BARRIER AGAINST RESERVOIR MATERIAL FLOW

CROSS REFERENCE TO RELATED U.S. APPLICATION DATA

The present application claims the benefit of provisional application 60/680,905 filed May 13, 2005 and provisional application 60/790,236 filed Apr. 7, 2006, both of which are incorporated by reference herein.

TECHNICAL FIELD

This invention relates to a multilayer drug delivery system. More particularly, the invention relates to a multilayer system that includes a barrier that separates layers in the system used in transdermal drug delivery.

BACKGROUND

Transdermal devices for the delivery of biologically active agents have been used for maintaining health and treating therapeutically a wide variety of ailments. For example, analgesics, steroids, etc., have been delivered with such devices. Such transdermal devices include patches in which a biologically active agent is delivered to the body tissue passively without the use of an additional energy source. Many such devices have been described, for example, in U.S. Pat. Nos. 3,598,122, 3,598,123, 4,379,454, 4,286,592, 4,314,557, 4,568,343, and U.S. Publication No. 20030026829, all of which are incorporated herein by reference.

A transdermal patch is typically a small adhesive bandage that contains the drug to be delivered. A simple type of such transdermal patches is an adhesive monolith including a drug-containing reservoir disposed on a backing. The reservoir is typically formed from a pharmaceutically acceptable pressure sensitive adhesive. In some cases, the reservoir can be formed from a non-adhesive material, with the skin-contacting surface having a thin layer of a suitable adhesive. The rate at which the drug is administered to the patient from these patches can vary due to normal person-to-person and skin site-to-skin site variations in the permeability of skin to the drug.

Figure 1:
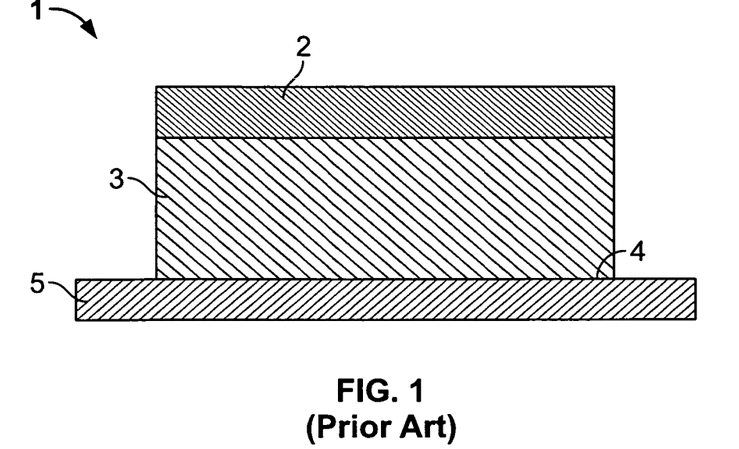
FIG. 1 illustrates a cross-section through a schematic, perspective view of a prior art transdermal therapeutic system.

More complex patches can be a multilaminate or can include drug reservoir layers in the patches. Exemplary transdermal drug delivery systems are illustrated by the embodiments shown in FIGS. 1, 2 and 3. As shown in FIG. 1, a transdermal monolithic patch 1 according to this invention has a backing layer 2, a drug reservoir 3 disposed on the backing layer 2, and a peelable (removable) protective layer 5. In the reservoir 3, which can be a layer, at least the skin-contacting surface 4 is an adhesive. The reservoir is a matrix (carrier) that is suitable for carrying the pharmaceutical agent (or drug) for transdermal delivery. The matrix is a structure in which the drug is or can be dissolved. Preferably, the whole matrix, with drugs and other optional ingredients, is a material that has the desired adhesive property. The reservoir 3 can be either a single phase polymeric composition or a multiple phase polymeric composition. In a single phase polymeric composition the drug and all other components are present at concentrations no greater than, and preferably less than, their saturation concentrations in the reservoir 3. This results in a composition in which no undissolved components are present. The reservoir 3 is formed using a pharmaceutically acceptable polymeric material that can provide adhesive property for application to the body surface. In a multiple phase polymeric composition, at least one component, for example, a therapeutic drug, is initially present in amount more than the saturation concentration. In some embodiments, more than one component, e.g., a drug and a permeation enhancer, is present in amounts above saturation concentration. In the embodiment shown in FIG. 1, the adhesive acts as the reservoir and includes a drug.

Figure 2:
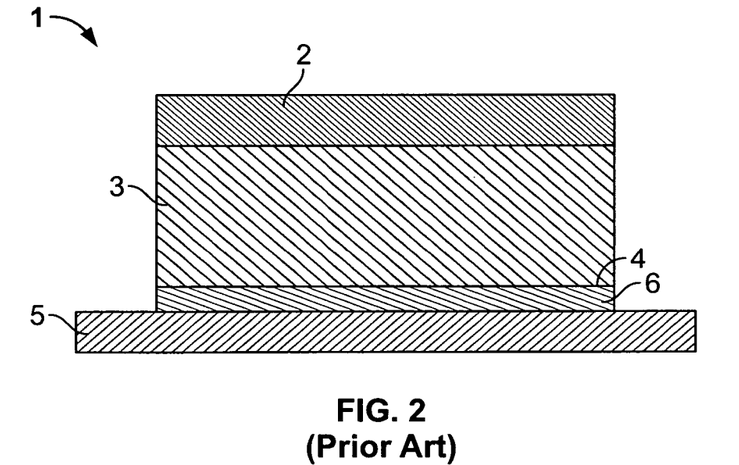
FIG. 2 illustrates a sectional view through another prior art transdermal therapeutic system.

In the embodiment shown in FIG. 2, the reservoir 3 is formed from a material that does not have adequate adhesive properties to maintain the patch on the skin for the desired period. In this embodiment of a monolithic patch 1, an overlaying adhesive layer 6 is included to attach the reservoir 3 to the skin. The reservoir 3 may be a single phase polymeric composition or a multiple phase polymeric composition as described earlier, except that it may or may not contain an adhesive with adequate adhesive bonding property for skin. The overlaying adhesive layer 6 can also contain the drug and permeation enhancer, as well as other ingredients. In this design, however, the drug in the reservoir 3 would have to pass through the adhesive layer 6 to reach the body surface. The solubility of the adhesive layer may not be suitable for the rate of delivery desired.

Figure 3:
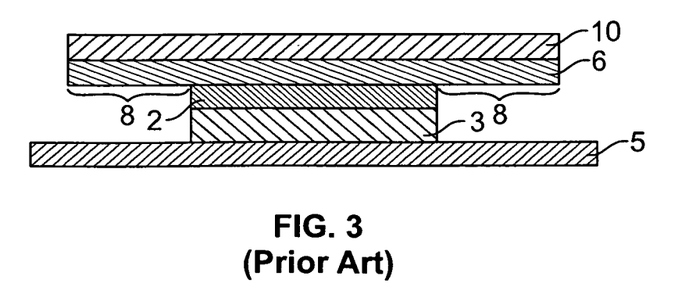
FIG. 3 illustrates a sectional view of a prior art system.

In an alternative prior device shown in FIG. 3, an adhesive layer 6 overlays the protective layer 2 and the reservoir 3 so as to adhere to the body surface with the overhanging portion 8 of the adhesive layer 6. A backing layer 10 protects the adhesive overlay layer 6.

Although the transdermal delivery of therapeutic agents has been the subject of intense research and development for over 30 years, only a relatively small number of drug molecules are suitable for transdermal delivery. For effective delivery, a delivery rate that is therapeutically effective is needed. Many factors affect the delivery rate. The thickness and concentration of the drug reservoir and the layers adjacent to the drug reservoir, as well as the rheological properties of the layers are some of these factors.

Often, due to the chemical as well as physical characteristics (e.g., Theological parameters), a system may change over time, e.g., during a period of storage. For example, the matrix formulations typically cold flow over time. The extent of cold flow can be affected by the fluid characteristics of the reservoir matrix, as well as physical forces that may be applied on the device, for example, by the protective pouch pressing on the reservoir. Typically, the drug delivery patches are made by cutting multiple layers simultaneously, resulting in the layers having the same planer size and their edges being flush on the side of the patch. Thus, for typical patch devices like those shown in FIG. 1 to FIG. 3, reservoir material may migrate along the side of the patch. In the cases of FIG. 1 and FIG. 2 the reservoir material may migrate and come into contact with the inside of a protective pouch, which is used for protecting the device and may not be chemically compatible with the drug reservoir. In the case of FIG. 3, the reservoir material may migrate to the adhesive layer 6. The adhesive layer 6 often is permeable to the drug in the reservoir, allowing the drug to diffuse throughout. If the adhesive contains chemicals to which the reservoir is permeable, the chemicals may migrate into the reservoir. Such unintended chemical migration is highly undesirable as it will reduce the concentration of the active agent in the drug reservoir and thus reduce the delivery rate, and may lead to contamination in the drug reservoir. Further, the inside surface of the protective pouch may contain heat seal polymers, which may allow drug migration from the reservoir. In the cases of FIG. 1 and FIG. 2, cold flow might still cause drug loss by diffusion to the heat seal material in the inside of the pouch. What is needed is a multilayer drug delivery system that is more stable overtime, thus ensuring reliable, predictable delivery of the drug, even for systems that may have been stored for a long period of time.

SUMMARY

The present invention provides a method and a device for delivery of biologically active agent or agents for therapeutic effects, especially delivery of the biologically active agents to a subject transdermally through the skin or other body surfaces. An individual can wear the device adhesively over an extended period of time.

In one aspect, the present invention provides a device for administration of a pharmaceutical agent to an individual at a therapeutically effective rate through a body surface. The device has a reservoir having a matrix including at least one pharmaceutical agent in the matrix; a backing layer attached to the reservoir and is substantially impermeable to the agent. There is also a second matrix in which the agent is diffusible and a barrier layer disposed between the reservoir and at least part of the second matrix. The barrier layer has a barrier outer perimeter and the reservoir has a reservoir outer perimeter such that the barrier layer outer perimeter is larger than the reservoir outer perimeter. The barrier layer is made of a material that is substantially impermeable, preferably completely impermeable, to the agent.

The barrier layer, having an outer perimeter larger than the outer perimeter of a drug reservoir attached to it, advantageously prevents any migration of the drug reservoir from crossing over to anther matrix layer.

The present invention is particularly useful in transdermal systems in which the reservoir material (matrix) is not so stiff that it is not flowable when pinched. In a method of making a patch with the reservoir material on the backing layer in which the two are cut to a desired size and shape, such as by die cutting, in which at least one (sometimes all) edge of the backing is flush with at least one edge of the reservoir matrix, some of the reservoir matrix material may attach to the edges of the backing layer. The edges of the reservoir and the backing layer are flush in FIG. 2 and FIG. 3. For example, when the cutting is done by cutting through the reservoir (matrix) and then the backing layer, the reservoir matrix, having a creep compliance that makes it somewhat flowable, will be pinched with the backing layer along the edges and some of the reservoir matrix material will be carried by the cutter to adhere to the edge (or edges) of the backing layer. When the resulting backing layer with reservoir matrix is attached to an adhesive (either that of a overlay or another reservoir matrix), the reservoir matrix material that adheres to the edge of the backing layer may touch the adhesive and allow drug to migrate thereto. Even if the two materials are only in close proximity but do not actually touch when the system is freshly made, with time, cold flow of the reservoir matrix or the adhesive will most likely allow them to touch and cause drug migration. Thus, the barrier layer of the present invention provides significant benefit to prevent the reservoir matrix and the adhesive from touching and drug migration therebetween.

In an aspect, the barrier layer is a frame-shaped layer. The frame-shaped layer has a window through which a matrix layer having some adhesive property can attach to a different layer, for example, the backing layer of another matrix layer. Since the reservoir material is fluid, this window enables the reservoir layer to be smaller in outer perimeter than the barrier frame and still be transferable and processed in the manufacturing process. In this way, a mechanized production line in which rolls (or webs) of materials are processed into final products can be implemented.

BRIEF DESCRIPTION OF THE DRAWINGS

The present invention is illustrated by way of example in embodiments and not limitation in the figures of the accompanying drawings in which like references indicate similar elements. The figures are not shown to scale unless indicated otherwise in context.

DETAILED DESCRIPTION

The present invention relates to delivery of pharmaceutical agents through a body surface (e.g. skin) involving the use of an reservoir that incorporates pharmaceutical agent (or drug) and optionally other ingredients and having an adhesive layer to maintain the delivery system on a body surface of an individual. In the present invention, a barrier layer is used to prevent the reservoir material with drug in its matrix to come into contact with another matrix in the device.

In describing the present invention, the following terms are to be used as indicated below. As used in this specification and the appended claims, the singular forms "a," "an" and "the" include plural references unless the content clearly dictates otherwise.

As used herein, the term "transdermal" refers to the use of skin, mucosa, and/or other body surfaces as a portal for the administration of drugs by topical application of the drug thereto for passage into the systemic circulation. Such passage can take place through intact surface (such as skin) without wounds or punctures.

"Biologically active agent" is to be construed in its broadest sense to mean any material that is intended to produce some biological, beneficial, therapeutic, or other intended effect, such as enhancing permeation, relief of pain and contraception.

As used herein, the term "drug" refers to any material that is intended to produce some biological, beneficial, therapeutic, or other intended effect, such as relief of pain and contraception.

As used herein, the term "therapeutically effective" refers to the amount of drug or the rate of drug administration needed to produce the desired therapeutic result.

Embodiments

Figure 4:
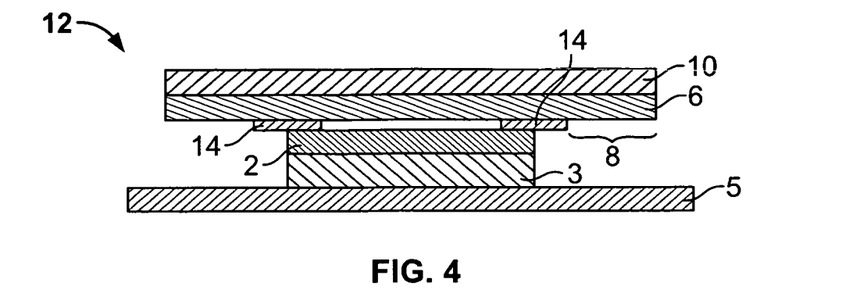
FIG. 4 illustrates a sectional view of a system of the present invention.

FIG. 4 shows an embodiment of the present invention. The transdermal drug delivery device 12 includes a drug reservoir 3 disposed on a backing layer 2, and a peelable (removable) protective layer 5 (or release liner). Upon use, the protective layer or release liner 5 is removed and the device is applied such that the reservoir is applied to the body surface. The reservoir 3 is a matrix (carrier) that is suitable for carrying the pharmaceutical agent (or drug) for transdermal delivery. Another matrix layer (which can be an adhesive layer) 6 is disposed more distal from the release liner 5. The matrix layer 6 can be a layer to provide adequate adhesion to a body surface to which the device is to be applied or to provide another agent for delivery to the body surface, or both. Another backing layer 10 is disposed on the matrix layer 6 and being more distal from the release liner 5. As used herein, a matrix layer can be a layer that contain a drug, an antagonist or can simply be an adhesive.

Figure 5:
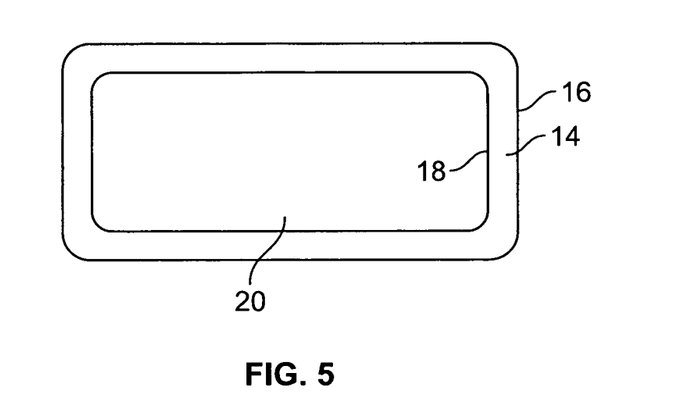
FIG. 5 illustrates a plan view of a barrier frame of a system of the present invention.
Figure 6:
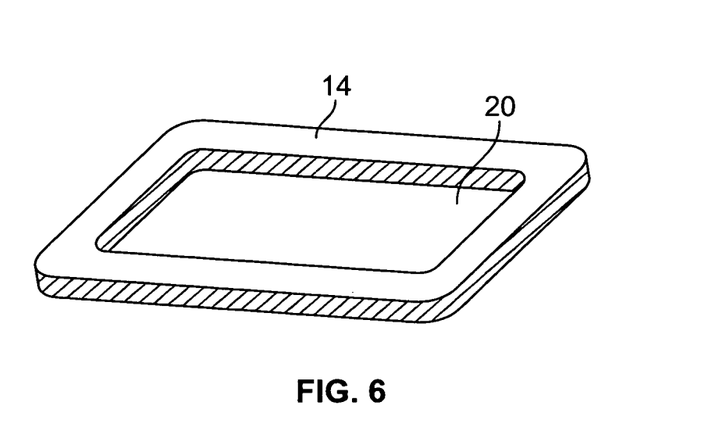
FIG. 6 illustrates an isometric perspective view of a barrier frame of a system of the present invention.
Figure 7:
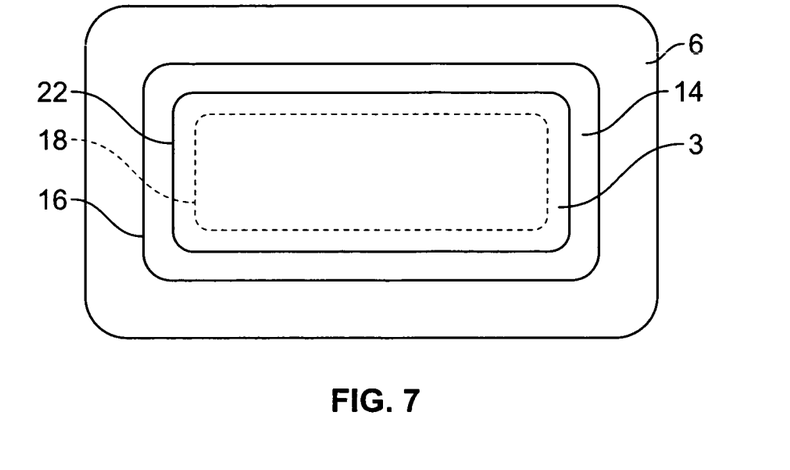
FIG. 7 illustrates a plan view of the system of FIG. 4 of the present invention.

For the sake of clarity and illustration the following will refer to the matrix layer 6 as an adhesive layer. A barrier frame 14 is disposed between the adhesive layer 6 and the backing layer 2 of the reservoir 3. FIG. 5 shows a top plan view of the barrier frame 14 and FIG. 6 shows an isometric perspective view of the barrier frame 14. The barrier frame 14 is frame shaped and has an outer perimeter 16 and an inner perimeter 18, which defines a window opening 20. FIG. 7 is a plan view looking from the viewpoint of the body surface at the device with the release liner 5 removed for the sake of clarity in the drawing. The reservoir 3 has an outer perimeter (or edge) 22 that is between the inner perimeter 18 and outer perimeter 16 of the barrier frame 14. The width (i.e., the distance between the inner perimeter 8 and outer perimeter 16) of the barrier frame 14 is selected, considering the cold flow characteristics and expected shelf life of the device, such that the barrier frame will prevent cold flow reservoir material to migrate past the outer perimeter 16. As used herein, the term "between" means only that something is in a position intermediate two other things and does not necessarily mean that it is immediately adjacent to them or contacting them, unless specified to be the case.

Medical devices and drugs typically have a time period before the expiration of which the device or drug is preferably to be used. For example, the regulatory filings for a medical device or drug at a relevant governmental agency would indicate such time periods. Such time periods can be considered to be the shelf life of a medical device or drug.

The overlay adhesive layer 6 is larger in area and in outer perimeter than the barrier frame 14. Thus, the overhang portion 8 outside of the frame 14 will provide adhesion to the body surface. The backing layer 10 is hidden by the overlay adhesive layer 6 and is therefore not shown. The figures are not shown to scale. In fact, the thicknesses of the various layers are relatively thin such that the device is flexible and generally flat when laid on a flat surface. Therefore, when pressure is applied to the flat surface of the device, either during manufacture or in use, the void area in the window is substantially filled so that the adhesive layer 6 attaches to the backing layer 2 within the window.

Figure 8:
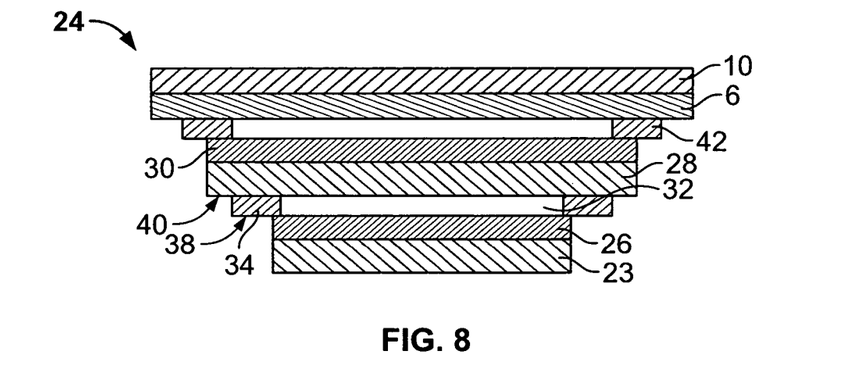
FIG. 8 illustrates a sectional view of another embodiment of a system of the present invention.

FIG. 8 illustrates another embodiment in which a transdermal drug delivery patch 24 has layers of matrixes and barrier frames layered in step progression. Each matrix layer, whether it is a reservoir or an adhesive, has a backing layer attached to the matrix layer on the side distal to the skin so that the matrix side faces toward the skin. Each matrix layer has the same surface area and a perimeter the same as those of the corresponding backing layer. The patch 24 has an adhesive overlay 6 attached to a backing layer 10. Most proximal to the skin is a first reservoir layer 23 with its backing layer 26 attached on the side of the reservoir layer 23 distal from the skin. A removable release liner (not shown for the sake of clarity of the drawing but is similar to that shown in FIG. 3 and FIG. 4) is on the reservoir side facing toward the skin. A second reservoir layer 28, with its backing layer 30, is disposed between (although not directly attached to) the overlay adhesive 6 (with its backing layer 10) and the first reservoir layer 23 (with its backing layer 26).

In FIG. 8, a first barrier frame 34 with a window opening 32 is disposed between and attached to the second reservoir layer 28 and the first reservoir backing layer 26. The outer perimeter of the second matrix layer 28 is larger than the outer perimeter of the first barrier frame 34, which in turn is larger than the outer perimeter of the first reservoir layer 23. The first barrier frame 34 has an inner perimeter, which forms the first window opening 32 that is smaller than the outer perimeter of the first reservoir 23. This way, the first barrier frame 34 has a ring of exposed area 38 (i.e., not covered by the backing layer 26) encircling the outer perimeters of the first reservoir layer 23 and its backing layer 26. This exposed area 38, of course, can be covered by a release liner before use, or covered by skin when in use. This exposed area 38 will prevent the first reservoir 23 to migrate to a position to contact the second reservoir layer 28.

The second reservoir layer 28 has a ring of exposed area 40 encircling the outer perimeters of the first barrier frame 34 and the first reservoir layer 23 such that upon application to the body surface at least a portion of the ring of exposed area 40 will contact the body surface for delivery of an agent from the second reservoir layer 28 to the tissue through the body surface. The agent will migrate from the more central part of the second reservoir layer 28 to the exposed area as the drug concentration changes upon delivery of the agent.

A second barrier frame 42 is disposed between and attached to the backing layer 30 of the second reservoir layer 28 and the overlay adhesive layer 6. Again, the perimeters of theses layers have a cascading relationship similar to the cascading relationship between the second reservoir layer 28, the first barrier frame 34 and the first reservoir layer 23. The overlay adhesive layer 6 has the largest outer perimeter among the matrixes and adhesives.

Figure 9:
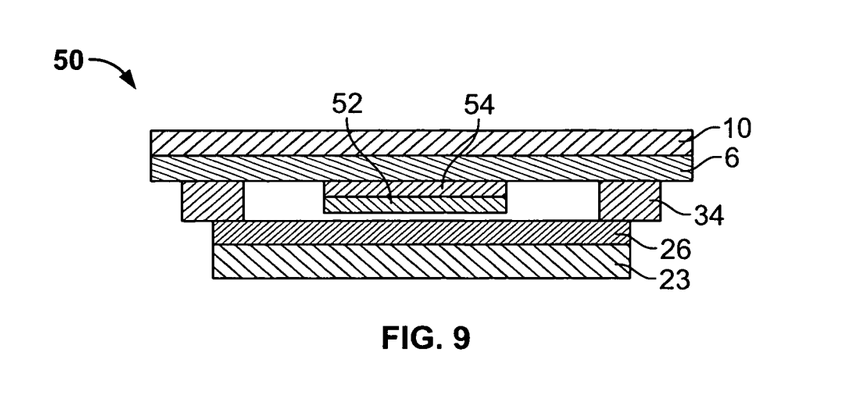
FIG. 9 illustrates a sectional view of yet another embodiment of a system of the present invention.

FIG. 9 illustrates an embodiment in which a second drug reservoir layer with a second drug wherein the second drug is not to be delivered during normal use of the device, or to be delivered only in a controlled or slowed rate. The multiple-drug device 50 has a first reservoir layer 23 with its backing layer 26, a barrier frame 34, and an overlay adhesive layer 6, with its backing layer 10, similar to those of the embodiments of FIG. 4 and FIG. 8. However, in the device of FIG. 9, a second reservoir layer 52, with it's backing layer 54, is disposed between the overlay adhesive layer 6 and the first reservoir layer 23. The backing layer 54 of the second reservoir layer 52 is attached to the overlay adhesive layer 6. The second reservoir layer 52 and it's backing layer 54 are encircled by the barrier frame 34. Thus, the second reservoir layer 52 is completely isolated within the window of the barrier frame 34. This device is particularly useful for containing antagonist drug(s) in the second layer to counter the effect of a first drug in the first reservoir layer 23. For example, if the drug in the first reservoir layer 23 is a narcotic, e.g., fentanyl, an antagonist drug, e.g., naltrexone, can be included in the second reservoir layer. In this embodiment or similar ones, under normal intended use, the user will not come into contact with the antagonist because the second reservoir layer 23 is not exposed. If an individual is exposed to the antagonist in the second reservoir layer 23, the antagonist would then exert a physiological effect on the individual. It is only when the device is subject to abuse, such as extraction by fluid or physical stress such as chewing, will the antagonist be released. A release liner on the first reservoir 23 is not shown for the sake of clarity of the drawing. Instead of an antagonist, an anti-abuse unpleasant agent that is foul-tasting (e.g., bitter, hot, peppery, or other un-welcomed taste) or which can cause unpleasant sensation (e.g., nauseating, etc.) can be placed in the second layer. For example, when a person chews on the device or takes a solvent extract from the device, the agent would give the person a very unpleasant sensation.

A method of manufacture and construction for a system containing an occluded counter acting agent (antagonist) as shown in FIG. 9 could consist of the following, assuming fentanyl and naltrexone-HCl are used as agonist and antagonist for illustration purposes:

Fentanyl base would be completely dissolved and mixed in a solution of solvent (such as ethyl acetate) and polyacrylate adhesive such as National Starch DURO-TACK 87-4287. The solution would be formulated so that the concentration of fentanyl would not exceed the solubility of fentanyl in the polymer (about 10%) once the solvent is removed. The solution would be coated to a uniform thickness on a 1-5 mil (0.025 mm-0.125 mm) thick silicone coated polyethylene terapthalate film (PET release coated liner) or similar. The liner and fentanyl polymer solution are passed through a series of ovens to remove the solvent forming a dry uniform film, typically less than 5 mils (0.125 mm) thick. The dried film would then be laminated to a second non-coated PET liner for further processing.

The antagonist layer would be produced by melting a polymer such as ethylene vinyl acetate (EVA-9, EVA-22, EVA-40, etc.), ethylene octene (ENGAGE), or similar elastomeric polymer, and blending in naltrexone-HCl at a concentration of 50-90%. The blend would be mixed to uniformity and extruded between two films such as PET liners, one of which would be release coated.

The two component films would be die cut and assembled on another polyisobutylene (PIB), polyacrylate, or similar adhesive (78) on a EVA/PET, polymer. fiber woven, (80) or similar overlay film in a converting operation as follows: Barrier frames (84) would be die cut from a 0.5-5 mil (0.0125 mm-0.125 mm) thick PET film such that the inner (18) and outer edges (16) were respectively slightly larger and smaller than the target matrix area (23,26) and uniformly spaced on the overlay adhesive (78). The naltrexone-EVA (52) on PET film (54) would be die cut to the target size and placed on the adhesive (6) within the inner boundary of the frames (34). The release coated liner would be removed in this assembly step.

The matrix film would be cut to the appropriate length and width (23,26) and placed on top of the barrier frames (34), completely isolating the naltrexone component (52).

Figure 10:
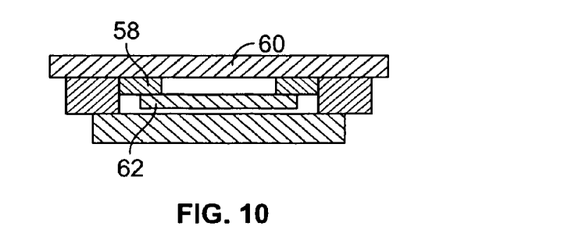
FIG. 10 illustrates a sectional view of another embodiment of a system of the present invention.

If desired, an additional barrier frame can be disposed between the second reservoir layer and the overlay adhesive layer. This is shown in FIG. 10, which for the sake of clarity of illustration shows a matrix layer and its corresponding backing layer as a single layer, represented by the matrix layer. In FIG. 10, a second barrier frame 58, having outer perimeter larger than the second reservoir layer 62, separates the overlay layer 60 and the second reservoir layer 62. Based on the above cascading design, further layers of matrixes and barriers can be included.

The drug (pharmaceutical agent) reservoir can be either a single phase polymeric composition or a multiple phase polymeric composition, as discussed earlier. In some embodiments, more than one component, e.g., a drug and a permeation enhancer, is present, and may be in amounts above saturation concentration. Preferably, the whole matrix, with drugs and other optional ingredients, is a material that has the desired adhesive properties, in which case, the reservoir 3 is formed using a pharmaceutically acceptable polymeric material that can provide adhesive property for application to the body surface.

The backing layers may be formed from any material suitable for making transdermal delivery patches, such as a breathable or occlusive material including fabric, polyvinyl acetate, polyvinylidene chloride, polyethylene, polypropylene, polyurethane, polyester, ethylene vinyl acetate (EVA), polyethylene terephthalate, polybutylene terephthalate, coated paper products, aluminum sheet and the like, and a combination thereof. In preferred embodiments, the backing layer includes low density polyethylene (LDPE) materials, medium density polyethylene (MDPE) materials or high density polyethylene (HDPE) materials, e.g., SARANEX (Dow Chemical, Midland, Mich.). The backing layer may be a monolithic or a multilaminate layer. In preferred embodiments, the backing layer is a multilaminate layer including nonlinear LDPE layer/linear LDPE layer/nonlinear LDPE layer. The backing layer preferably has a thickness of about 0.012 mm (0.5 mil) to about 0.125 mm (5 mil); more preferably 0.025 mm (1 mil) to about 0.1 mm (4 mil); even more preferably 0.0625 mm (1.5 mil) to about 0.0875 mm (3.5 mil).

The purpose of the barrier frame is to separate materials, therefore the active compounds, excipients, and polymers within the system should have negligible solubility or permeability in the barrier material. It is desirable for the barrier material to serve as a processing web during assembly, thus mechanical strength (i.e. inelastic) in the web direction may be desirable. Further, the barrier frame may be used as a separating point in some system designs, therefore it may be release coated on one or both sides of the barrier frame. Materials that can be used for making a barrier frame include, for example, polyethylene terapthalate (PET) film, polyvinyl acetate, polyvinylidene chloride, polyethylene, polypropylene, polyurethane, polyester, polybutylene terephthalate, coated paper products, aluminum sheet and the like, and any combination thereof. The thickness of the barrier layer (e.g., barrier frame) preferably ranges between 0.012 mm (0.5 mil) and 0.125 mm (5.0 mil), with or without release coating on either side. Other materials can be used, as long as the active agent or permeation enhancers are insoluble in them.

The reservoir or matrix may be formed from drug (or biological active agent) reservoir materials as known in the art. For example, the drug reservoir is formed from a polymeric material in which the drug has reasonable solubility for the drug to be delivered within the desired range, such as, a polyurethane, ethylene/vinyl acetate copolymer (EVA), acrylate, styrenic block copolymer, and the like. In preferred embodiments, the reservoir 3 is formed from a pharmaceutically acceptable pressure sensitive adhesive, preferably an acrylate copolymer-based adhesive, as described in greater detail below.

The adhesive reservoir 3 may be formed from standard pressure sensitive adhesives. Examples of known pressure sensitive adhesives include, but are not limited to, acrylates, polysiloxanes, polyisobutylene (PIB), polyisoprene, polybutadiene, styrenic block polymers, and the like. Examples of styrenic block copolymer-based adhesives include, but are not limited to, styrene-isoprene-styrene block copolymer (SIS), styrene-butadiene-styrene copolymer (SBS), styrene-ethylenebutene-styrene copolymers (SEBS), and di-block analogs thereof. PIB generally has poorer solubility for drugs than acrylate adhesives. Thus, acrylate polymers are preferred as the matrix for drug reservoirs but either PIB or acrylates are preferred as an overlay adhesive layer. The drug reservoir or the matrix layer can have a thickness of 0.025-0.25 mm (1-10 mils), preferably 0.05-0.12 mm (2-5 mils), more preferably 0.05-0.075 mm (2-3 mils).

It is desired that the material for the matrix in the reservoir has a high solubility for the agent to be delivered through the body surface, either for therapeutic drug agents or permeation enhancers to facilitate the delivery. If the reservoir material does not provide adequate adhesiveness for multiple day use, the overlay adhesive layer should be made with an adhesive material that has stronger and sufficient adhesive and cohesive properties for multiple day application.

Preferred materials for making the reservoir or overlay adhesive coating according to the present invention include acrylates, which can be a copolymer of various monomers ("soft" monomer, "hard" monomer, and "functional" monomer) or blends of copolymers. Acrylic polymers provide good solubility for many agents. The acrylic polymers can be composed of a copolymer or terpolymer including at least two or more exemplary components selected from the group including acrylic acids, alkyl acrylates, methacrylates, copolymerizable secondary monomers or monomers with functional groups. Functional monomers are often used to either provide needed functionality or improve cohesive properties through grafting or cross-linking. Examples of functional monomers are acids, e.g. acrylic acid, methacrylic acid and hydroxy-containing monomers such as hydroxyethyl acrylate, hydroxypropyl acrylate, acrylamides or methacrylamides that contain amino group and amino alcohols with amino group protected. Functional groups, such as acid and hydroxyl moieties can also help to increase the solubility of basic ingredients (e.g., drugs) in the polymeric material. Additional useful "soft" and "hard" monomers include, but are not limited to, methoxyethyl acrylate, ethyl acrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, hydroxyethyl acrylate, hydroxypropyl acrylate, vinyl acetate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxyethyl acrylate, methoxyethyl methacrylate, and the like. Additional examples of appropriate acrylic adhesives suitable in the practice of the invention are described in Satas, "Acrylic Adhesives," Handbook of pressure-Sensitive Adhesive Technology, 2nd ed., pp. 396-456 (D. Satas, ed.), Van Nostrand-Reinhold, New York (1989). The acrylic adhesives are commercially available (National Starch and Chemical Corporation, Bridgewater, N.J.; Solutia, Mass.). Further examples of acrylate-based adhesives are as follows, identified as product numbers, manufactured by National Starch (Product Bulletin, 2000): Duro-Tak® 87-4098, 87-2287, 87-4287, 87-2051, 87-2052, 87-2054, 87-2196, 87-9259, 87-9261, 87-2979, 87-2510, 87-2353, 87-2100, 87-2852, 87-2074, 87-2258, 87-9085, 87-2525, 87-2825, 87-200A, 87-201A, 87-2194, 87-2677, 87-900A, and 87-9301. Duro-Tak® 87-2287 and 87-4287 both are polymeric adhesive having similar monomer compositions: 5.2 wt % 2-hydroxyethyl acrylate monomer, about 20-40 wt % vinyl acetate, and about 55-75 wt % 2-ethylhexyl acrylate; and these two polymeric adhesives are provided solubilized in ethyl acetate in solids content of about 40-50 wt %. The Duro-Tak® 87-2287 adhesive is also mentioned in U.S. Pat. No. 5,693,335.

The acrylic polymers can include cross-linked and non-cross-linked polymers. The polymers can be cross-linked by known methods to provide the desired polymers. In some typical embodiments, the adhesive at the stage of application to the skin is a acrylate adhesive having a glass transition temperature ($T_g$) less than $-10°$ C., preferably $-10°$ C. to about $-30°$ C., more preferably having a $T_g$ of about $-20°$ C. to about $-40°$ C. The molecular weight of the acrylate adhesive, expressed as weight average (MW), preferably ranges from 25,000 to 10,000,000, further preferably from 50,000 to about 3,000,000 and more preferably from 100,000 to 1,000,000 prior to any cross-linking reactions. Upon cross-linking the MW can further increase, as known to those involved in the art of polymer chemistry.

As aforementioned, the reservoir(s) can include a multiple phase composition or a single phase polymeric composition, free of undissolved components, containing an amount of the drug sufficient to induce and maintain the desired therapeutic effect in a human for at least three days. The present invention has utility in connection with the delivery of drugs within the broad class normally delivered through body surfaces and membranes, including skin. In general, this includes therapeutic agents in all of the major areas, including, but not limited to, ACE inhibitors, adenohypophoseal hormones, adrenergic neuron blocking agents, adrenocortical steroids, inhibitors of the biosynthesis of adrenocortical steroids, alpha-adrenergic agonists, alpha-adrenergic antagonists, selective alpha-two-adrenergic agonists, analgesics, antipyretics and anti-inflammatory agents, androgens, local and general anesthetics, antiaddictive agents, antiandrogens, antiarrhythmic agents, antiasthmatic agents, anticholinergic agents, anticholinesterase agents, anticoagulants, antidiabetic agents, antidiarrheal agents, antidiuretic, antiemetic and prokinetic agents, antiepileptic agents, antiestrogens, antifungal agents, antihypertensive agents, antimicrobial agents, antimigraine agents, antimuscarinic agents, antineoplastic agents, antiparasitic agents, antiparkinson's agents, antiplatelet agents, antiprogestins, antischizophrenia agents, antithyroid agents, antitussives, antiviral agents, atypical antidepressants, azaspirodecanediones, barbituates, benzodiazepines, benzothiadiazides, beta-adrenergic agonists, beta-adrenergic antagonists, selective beta-one-adrenergic antagonists, selective beta-two-adrenergic agonists, bile salts, agents affecting volume and composition of body fluids, butyrophenones, agents affecting calcification, calcium channel blockers, cardiovascular drugs, catecholamines and sympathomimetic drugs, cholinergic agonists, cholinesterase reactivators, contraceptive agents, dermatological agents, diphenylbutylpiperidines, diuretics, ergot alkaloids, estrogens, ganglionic blocking agents, ganglionic stimulating agents, hydantoins, agents for control of gastric acidity and treatment of peptic ulcers, hematopoietic agents, histamines, histamine antagonists, hormones, 5-hydroxytryptamine antagonists, drugs for the treatment of hyperlipoproteinemia, hypnotics and sedatives, immunosupressive agents, laxatives, methylxanthines, moncamine oxidase inhibitors, neuromuscular blocking agents, organic nitrates, opiod analgesics and antagonists, pancreatic enzymes, phenothiazines, progestins, prostaglandins, agents for the treatment of psychiatric disorders, retinoids, sodium channel blockers, agents for spasticity and acute muscle spasms, succinimides, thioxanthines, thrombolytic agents, thyroid agents, tricyclic antidepressants, inhibitors of tubular transport of organic compounds, drugs affecting uterine motility, vasodilators, vitamins and the like, alone or in combination. Basic drugs such as opioids (e.g., fentanyl and analogs: alfentanil, carfentanil, lofentanil, remifentanil, sufentanil, trefentanil, and the like), galanthamine (or galantamine), and the salts of such basic drugs are well suited to be incorporated in the matrix with the acrylate polymer. Antagonist drugs for fentanyl, its analogs, and the salts thereof include amiphenazole, naltrexone, methylnaltrexone, naloxone, nalbuphine, nalorphine, nalorphine dinicotinate, nalmefene, nadide, levallorphan, cyclozocine and pharmaceutically acceptable salts thereof. Such antagonists can be included, for example, in a second reservoir layer in the present invention, in which the second reservoir is not in contact of the body surface. Narcotic agonists and their antagonists, including their salts, esters, functional and structural analogs are known to those skilled in the art.

As indicated in the above, in some embodiments, the reservoir or the adhesive may contain additional components such as, additives, permeation enhancers, stabilizers, dyes, diluents, plasticizer, tackifying agent, pigments, carriers, inert fillers, antioxidants, excipients, gelling agents, anti-irritants, vasoconstrictors and other materials as are generally known to the transdermal art. Typically, such materials are present below saturation concentration in the reservoir.

The protective layer (or release liner) can be made of a polymeric material that may be optionally metallized. Examples of the polymeric materials include polyurethane, polyvinyl acetate, polyvinylidene chloride, polypropylene, polycarbonate, polystyrene, polyethylene, polyethylene terephthalate, polybutylene terephthalate, paper, and the like, and a combination thereof. In preferred embodiments, the protective layer includes a siliconized polyester sheet.

A wide variety of materials that can be used for fabricating the various layers of the drug delivery patches according to this invention have been described above. This invention therefore contemplates the use of materials other than those specifically disclosed herein, including those which may hereafter become known to the art to be capable of performing the necessary functions.

Administration of the Drug

On application to the skin, the drug in the drug reservoir of the transdermal patch diffuses into the skin where it is absorbed into the bloodstream to produce a systemic therapeutic effect. The onset of the therapeutic depends on various factors, such as, potency of the drug, the solubility and diffusivity of the drug in the skin, thickness of the skin, concentration of the drug within the skin application site, concentration of the drug in the drug reservoir, and the like (see e.g., U.S. Pat. No. 4,588,580 for a discussion of relative permeabilities and potencies of fentanyl and analogs thereof). Typically, it is preferable that a patient experiences an adequate effect within a few hours (e.g., 3-6 hours) of initial application. However, this is significant only on the initial application. On repeated sequential application, the residual drug in the application site of the patch is absorbed by the body at approximately the same rate as the drug from the new patch is absorbed into the new application area. Thus the patient should not experience any interruption of the therapeutic effect, such as analgesia.

When continuous therapeutic effect is desired the depleted patch would be removed and a fresh patch is applied to a new location. For example, the patch would be sequentially removed and replaced with a fresh patch at the end of the administration period to provide continual therapeutic effect, such as in the use of analgesics for the relief of chronic pain. Since absorption of the drug from the fresh patch into the new application area usually occurs at substantially the same rate as absorption by the body of the residual drug within the previous application site of the patch, blood levels will remain substantially constant. Additionally, it is contemplated that doses may be increased over time and that concurrent use of other drugs may occur to deal with a need for increased relief.

Depending on the drug to be delivered, administration of a patch can be maintained for a few days, e.g., at least three days, and up to 14 days, preferably to 3-7 days, the 3-4 day regimen being considered more preferable. In certain preferred embodiments, at least 3%, but not more than 40%, of the total amount of the drug in the patch is administered during approximately the first 24 hours of use; at least 6%, but not more than 50%, of the total amount of the drug is administered during approximately the first 48 hours of use; and at least 10%, but not more than 75%, of the total amount of the drug is administered during the administration period.

Methods of Manufacture

The transdermal devices are made from laminates which are manufactured according to known methodology. In general, in an embodiment, a solution of the polymeric reservoir material, as described above, is added to a mixer, with the desired amounts of the drug, permeation enhancers, and other ingredients that may be needed. Preferably, the polymeric reservoir material is an acrylate material to provide adhesive property to the transdermal delivery device. Typically, the acrylate material is solubilized in an organic solvent, e.g., ethanol, ethyl acetate, hexane, and the like. The mixer is then activated for a period of time to achieve acceptable uniformity of the ingredients. The mixer is attached by means of connectors to a suitable casting die located at one end of a casting/film drying line. The mixer is pressurized using nitrogen to feed solution to the casting die. Optionally the solution is transferred to a pressurizable tank. Solution is cast as a wet film onto a moving siliconized polyester web. The web is drawn through a series of ovens to evaporate the casting solvent to acceptable residual limits. The dried reservoir film is then laminated to a selected backing membrane and the laminate is wound into rolls. However, the materials may also be dry blended and extruded to produce a similar laminate. In subsequent operations, the laminate is further processes in conjunction with other laminate(s) to result in individual patches that are die-cut, separated and unit-packaged using suitable pouchstock. Laminates of other reservoir materials can be made by people skilled in the art.

The present invention is particularly adapted for mass manufacturing practices using mechanized automated machineries. In such manufacture practices, long rolls (can be considered to be long strips) or webs of laminate materials are fed through roller nips for further lamination to complete the assembly and dies for cutting and alignment. For practical mechanical handling, such webs can be considered to be continuous. Thus, a reservoir, or matrix material needs to have a backing or some kind of flexible but strong (tough and not easily torn) material attached to it for ease of transfer. In this way, rolls of materials can be processed without tearing.

FIGS. 11 to 14 illustrate how mass production by machines involving repetitive mechanical die-cutting and pressing processes are used to make exemplary patches such as those of FIG. 4. The repetitive mechanical die-cutting is done in cycles of motion as in most computer or process-controlled machines. In this embodiment of the method, the dies are rotary dies. Cut pieces can be picked up by suction (or vacuum). Left over scrap material (which may have a ladder shape when center pieces are taken out) is pulled into an uptake.

Typically, the manufacture of a product of an embodiment similar to that shown in FIG. 4 involves two laminates. The drug/adhesive matrix is located between a PET film and a release liner in a laminate. The overlay laminate has another adhesive layer between a backing and a release liner. A PET film is used for the barrier layer also. Four payouts will be required, one for each laminate, one for the PET barrier film, and one for the final release liner. In this embodiment, six take-ups are used, one for the temporary liner from the overlay laminate, one for the barrier frame scrap, one for the drug laminate edge trim, one for the temporary liner from the drug/matrix laminate, one for the overlay scrap, and one for the final die-cut product. Four dies are used to produce the finished assembly as follows.

Figure 11:
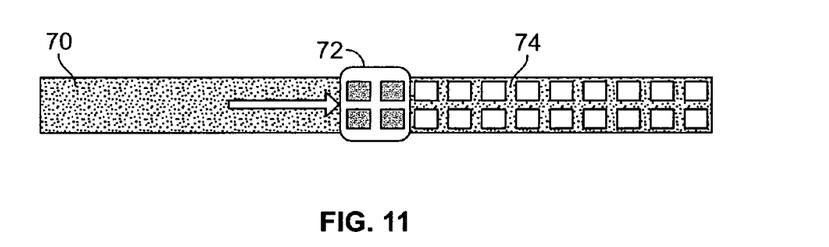
FIG. 11 illustrates a schematic view of a manufacturing step in an embodiment of manufacturing according to the present invention.

FIG. 11 shows a schematic view of how a rotary vacuum die 72 in which a PET film 70 payout (payout #1) is fed into a die station 72 where a square or rounded barrier "frame" similar to that shown in FIG. 5 and FIG. 6 is cut, carried, and placed in a registered position onto the adhesive side of an overlay laminate. The barrier frames are not shown in FIG. 11 as they are carried around the die by vacuum. The left over scrap 74 is taken away from the die 72 by take up #1.

Figure 12:
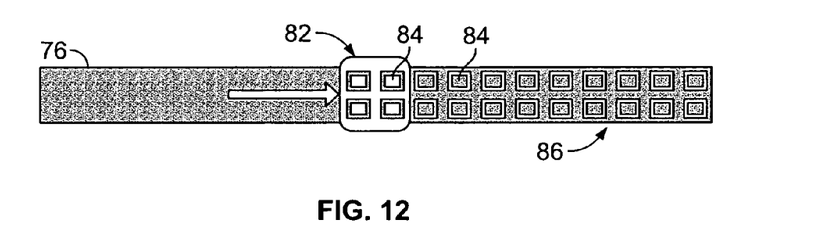
FIG. 12 illustrates a schematic view of a manufacturing step in an embodiment of manufacturing according to the present invention.
Figure 13:
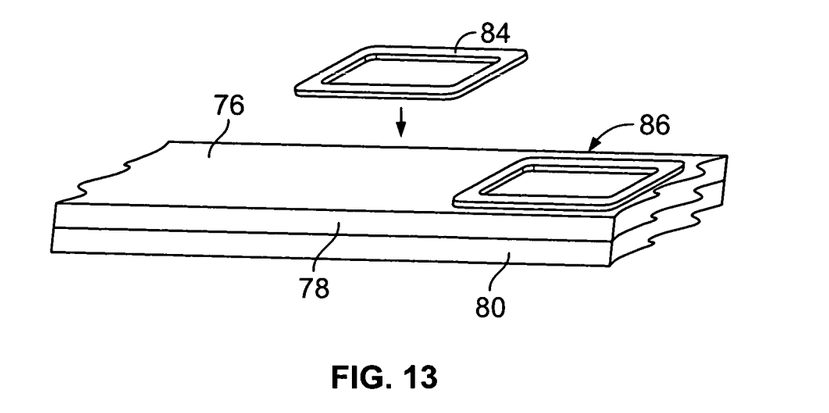
FIG. 13 illustrates a schematic perspective view of a manufacturing step in an embodiment of manufacturing according to the present invention.

An adhesive laminate (which includes siliconized PET temporary liner protecting an adhesive on a backing layer) is paid out from payout #2 and the temporary release liner is stripped to result in just a continuous strip of adhesive on a backing. The scrap release liner is removed by take up #2 (not shown). FIG. 12 shows the web 76 of the adhesive having an adhesive layer 78 on a backing layer 80 being fed to a rotary die 82 that applies the barrier frames 84 on the adhesive side of the strip 76, as shown by FIG. 13, forming a web of adhesive overlays 86. The window in a barrier frame 84 advantageously allows the adhesive material of the adhesive layer 78 to later attach to the backing of a cut discrete unit of the reservoir layer, thus, facilitating the mechanized transferring and application of the reservoir layer.

Figure 14:
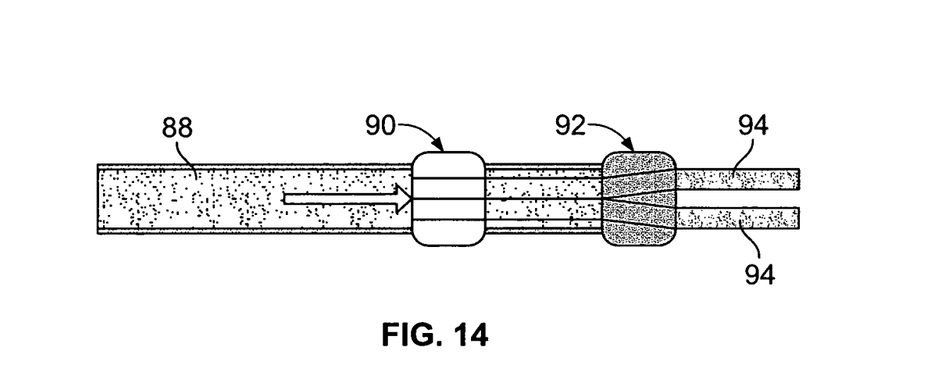
FIG. 14 illustrates a schematic view of a manufacturing step in an embodiment of manufacturing according to the present invention.

As shown in FIG. 14, a continuous strip 88 of drug/adhesive matrix (reservoir) is paid out (payout #3) to a rotary slitting die 90 to be slit and spread by a spreader 92 to the appropriate width so that the slit strips 94 can be spread and aligned to the adhesive overlay layer 86, which can be made of, e.g., PIB. The edges of the continuous strip 88 are also trimmed to result in a suitable width that facilitates forming the adhesive units that correspond to the barrier frames later. The edge trim is cut and removed (take-up #3, which is not shown in FIG. 14).

Figure 15:
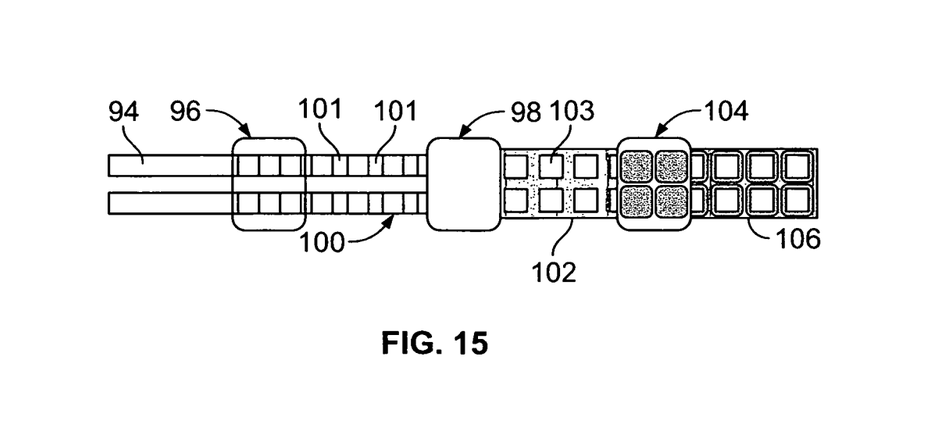
FIG. 15 illustrates a schematic view of a manufacturing step in an embodiment of manufacturing according to the present invention.

FIG. 15 shows how the system web is combined with the slit strip 94 adhesive web. The system die 96 cuts the slit web 94 to discrete system units of drug reservoir and backing of the desired length. The discrete system units are lifted from the temporary liner on which they were carried. Leftover temporary liner (not shown in the diagram) is carried off as take up #4. The discrete units 101 of system reservoir/backing are then spaced, transferred, and laminated to the final liner 100 from payout #4 (not shown).

A lamination roller 98 applies the drug reservoir units on the final liner 100 to the adhesive overlay 86. The system webs (i.e., the webs with the drug reservoir) and overlay web are joined such that the system edges fall within the center of the "frames" on the overlay. Since the barrier frames 84 are discrete units spaced apart on the adhesive overlay 86 the slit strip 94 has to similarly space the drug reservoirs on the final liner 100 from payout #4. This is accomplished by having only intermittent contact between the slit strip and the final liner at die 96. The final liner web is accelerated when not in contact with the die 96, and decelerated to match the die speed for the duration of the contact, creating the spacing. This results in a web 102 with discrete units 103 of drug reservoirs 3 attached to backing layers 2 and barrier frames 84, which are shown in FIG. 15. The web 102 is then kiss cut by die 104 through the overlay adhesive to define the overlay dimensions and the excess adhesive is removed (take up #5). The resulting strip 106 is collected (take-up #6), and can then be cut, fed between two strips of protective material, sealed, and cut into individual pouches containing the devices.

Figure 16:
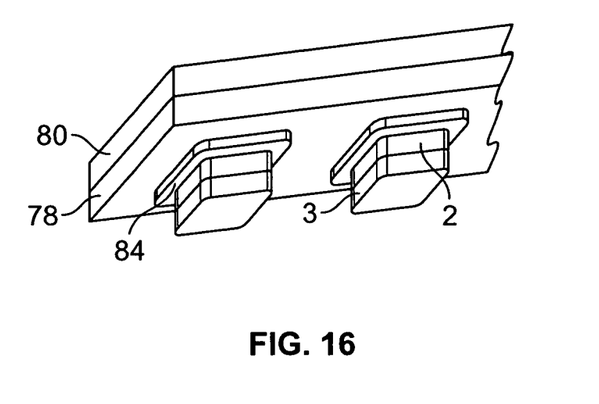
FIG. 16 illustrates an isometric perspective view of a partially finished product in an embodiment of manufacturing process according to the present invention.
Figure 17:
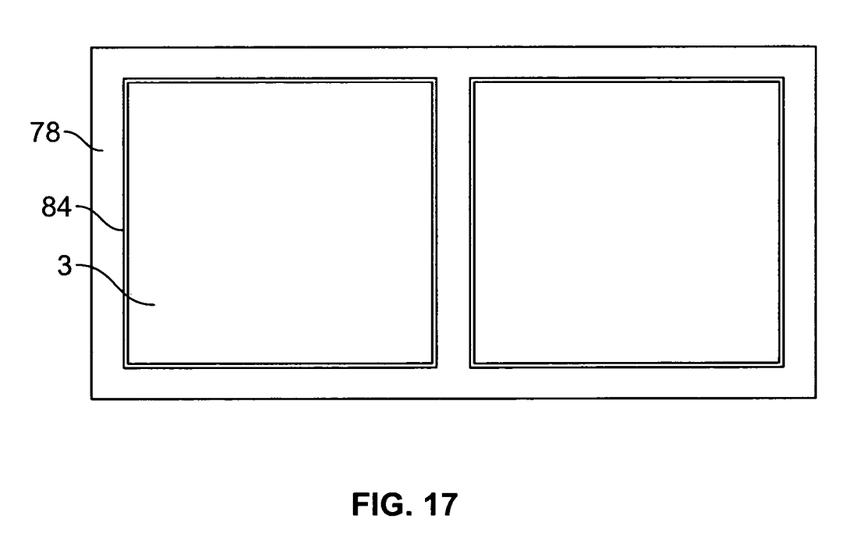
FIG. 17 illustrates a plan view of an embodiment of a transdermal drug delivery patch according to the present invention.

The patches can be made such that only one reservoir matrix island in on a patch, similar to the patch of FIG. 4. However, the transdermal drug delivery systems (patches) can be cut in such a way that two or more islands of reservoir matrix can be present on a single patch, as shown in FIG. 17 (showing an example of two islands), which can be made if the configuration of FIG. 16 is cut to include multiple islands. Between the islands is a space allowing the adhesive from the overlay to show through to aid adhesion to the skin. When such a patch is applied to an individual, the area between the active matrixes would provide additional adhesion maximizing skin contact and therefore flux. This design increases average skin contact for extended wear of large highly loaded adhesives, in which adhesion usually decreases as the components leave the system and or moisture is absorbed.

EXAMPLES

Below are examples of specific embodiments for carrying out the present invention. The examples are offered for illustrative purposes only, and are not intended to limit the scope of the present invention in any way.

Example 1

Barrier Frame Application, in Which Active Pharmaceutical Ingredient is Galantamine A galantamine-containing polyacrylate adhesive solution is mixed with flux enhancing agents such as lauryl pyrollidone, oleic acid, lauryl lactate. The adhesive is a National Starch Duro-tak® 87-4287 adhesive which is a polymerization product of vinyl acetate, 2-ethylhexyl acrylate, and hydroxyethyl acrylate. The solution is film cast to approximately 9 mils (0.225 mm) thick on a 2 mil (0.05 mm) or 3 mil (0.075 mm) siliconized polyethelene terepathalate (Si-PET) film (also known as release liner) and dried according to conventional technology. Once the solvents are removed, the resulting film is approximately 5 mils (0.125 mm) thick and has approximately 14 wt % galantamine. The adhesive film is then laminated to the PET side of a 2 mil PET/EVA (ethylene vinyl acetate) backing film. All the components within the drug adhesive are typically below their saturation concentration and are referred to as a matrix.

A PIB adhesive film is prepared separately in similar fashion by mixing 2 grades of poly isobutylene, with polybutene, and crospovidone in heptane. The solution is film cast at approximately 6 mils (0.15 mm) onto a 3 mil (0.075 mm) Si-PET (silicone coated PET) film, dried to 3 mils (0.075 mm) as above, and laminated to a polyester interlock fabric.

Both the drug matrix film and the PIB adhesive films are simultaneously mounted on a web converting machine along with an uncoated 1-2 mil (0.025 mm-0.05 mm) PET film from which the barrier frames are cut and a 3 mil (0.075 mm) Si-PET film which will be used as the final system liner.

The following steps describe the order of assembly of an individual system, however all steps occur continuously in various locations throughout the machine in a web converting process. The individual product system assembled in this example has an active area of 48 cm$^2$, centered on a barrier frame, centered on a PIB adhesive of 60 cm$^2$ all covered by a release liner.

1. The release liner is peeled (stripped) from the PIB adhesive laminate.
2. The uncoated PET film is fed through a rotary die, cutting both the inner and outer perimeter of the frame to the desired dimensions. The frame outer perimeter and inner perimeter dimensions are approximately ±0.1 inches (2.54 mm) of the perimeter of the active area (i.e., the drug reservoir area) of the finished product.
3. The frame and center are carried by vacuum around the rotary die where the center piece is blown off and removed by a second vacuum.
4. The remaining frame is transferred to the adhesive surface of the PIB film of step 1.
5. The drug matrix is slit and spread to align with the frames on the PIB web.
6. The drug matrix webs are passed through a rotary die where systems are kiss cut (cuts through the backing and drug matrix, but not the liner) and singulated from the web and carried by vacuum around the rotary die where the system is placed on the final liner at a spacing consistent with the barrier frames on the overlay adhesive.
7. The system web is laminated to the PIB web with the systems placed on the centers of the frames.
8. A final system die cuts the PIB backing and removes the excess overlay adhesive.
9. The product web is collected and is then ready for packaging.

Example 2

Barrier Frame Insert Application Having Fentanyl

A fentanyl (API) containing adhesive solution is mixed. The adhesive is a National Starch Duro-tak® 87-4287 adhesive. The solution is film cast to approximately 4 mils (0.1 mm) thick on a 3 mil (0.075 mm) Si-PET film and dried according to conventional technology. Once the solvent is removed, the resulting film is approximately 2 mils (0.05 mm) thick and consists of approximately 8% fentanyl. The adhesive film is then laminated to a 2 mil uncoated PET film.

A second adhesive film (PIB) is prepared in a similar manner to the previous example and laminated to a 1 mil (0.025 mm) release liner. The 1 mil liner is then removed and the adhesive is laminated to the 2 mil liner of the drug matrix laminate.

An antagonist film is prepared separately by melting and extruding a mixture of naltrexone and EVA. The components are continuously added at the correct weight ratio to an extruder that heats and mixes the blend into a homogenous fluid. The liquid is passed through a slot die onto a moving web of 3 mil (0.075 mm) Si-PET, a 1 mil (0.025 mm) Si-PET web is laminated and the film is cooled and calendared to a solid of the desired thickness.

Both the drug matrix film and the antagonist films are simultaneously mounted on a web converting machine along with an uncoated 1-2 mil (0.025 mm to 0.05 mm) PET film from which the barrier frames are cut and a 2 mil PET/EVA film which will be used as the final system liner.

The following steps describe the order of assembly of an individual system, however all steps occur continuously in various locations throughout the machine in a web converting process. The system assembled in this example consists of an active area of 40 cm$^2$, centered on a barrier frame containing a 20 cm$^2$ antagonist area covered with a PET/EVA backing film.

1. The release liner is peeled (stripped) from the PIB adhesive side of the drug matrix laminate.
2. The uncoated PET is fed through a rotary die, cutting both the inner and outer perimeter of the frame to the desired dimensions, at the spacing of the finished product. The frame outer dimensions are approximately 0.2 inch (0.51 cm) smaller than the active area of the finished product. The inner dimensions are approximately 0.2 inch (0.51 cm) smaller than the outer frame dimensions.
3. The frame and center are carried by vacuum around the rotary die where the center piece is blown off and removed by a second vacuum.
4. The remaining frame is transferred to the adhesive surface of the PIB film of step 1.
5. The antagonist film is slit and spread to align with the frames on the drug matrix web.
6. The 3 mil (0.075 mm) liner is stripped from the antagonist film.
7. The antagonist film is carried through a rotary die where the systems are singulated from the web and transferred by vacuum to the centers of the frames on the frame adhesive web of step 4 (The remaining 1 mil liner contacts the adhesive).
8. The PET side of a PET/EVA backing film is laminated on top of the naltrexone/ frame side of the system.
9. A final system die kiss cuts through the backing film, and down through the drug matrix to the 3 mil Si-PET film to the final system size. The scrap is collected on a takeup.
10. The product web is collected on a takeup and is then ready for packaging.

Example 3

A Transdermal Galantamine System with Galantamine Matrix Islands

The individual product system assembled in this example has two active areas (islands) of 20 cm$^2$, centered on barrier frames, evenly spaced on a PIB adhesive of 60 cm$^2$, all covered by a release liner.

A transdermal galantamine system is to be made through a construction showed in FIGS. 16 and 17. Multiple frames and matrixes with galantamine would be assembled on a single system applicable to a patient, for example, having a configuration like that of FIGS. 16 and 17. This design increases average skin contact for extended wear of large highly loaded adhesives, in which adhesion usually decreases as the components leave the system and or moisture is absorbed. The area between the active matrixes would provide additional adhesion maximizing skin contact and therefore flux.

Galantamine is mixed into solution of solvent (ethyl acetate) and polyacrylate adhesive such as National Starch DURO-TAK 87-4287 with permeation enhancers. The solution is formulated so that the concentration of galantamine is about 5 wt % and does not exceed its solubility in the polymer once the solvent is removed. The solution is coated to a uniform thickness on a 5 mil (0.125 mm) thick silicone coated polyethylene terephthalate film (PET release coated liner) or similar. The liner and galantamine polymer solution are passed through a series of ovens to remove the solvent forming a dry uniform film, to less than 5 mil (0.125 mm) thick. The dried film is then laminated to a second non-coated PET liner for further processing. The active component film is die cut and assembled on another polyisobutylene (PIB) adhesive (although other adhesives, e.g., polyacrylate, or similar adhesive can be used) (78) on a EVA/PET overlay film (80) in a converting operation as follows:

Barrier frames (84) is die cut from a 1 mil (0.025 mm) thick PET film such that the inner (18) and outer edges (16) are 0.15 cm larger and smaller than the target matrix area (3) and spaced according to adhesion requirements on the overlay adhesive (78) 5.15 cm apart in this example.

The matrix film is cut to the appropriate length and width 4.5×4.5 cm and placed on top of the barrier frames (84). The matrix layer release coated liner is removed in this assembly step and replaced with a larger final system release liner (not shown in the figure), covering all the system components. The assembled system is then die cut to the appropriate size with two separate skin-contacting reservoirs on a single patch applicable to a patient.

The practice of the present invention will employ, unless otherwise indicated, conventional methods used by those in pharmaceutical product development within the knowledge of those skilled in the art. Embodiments of the present invention have been described with specificity. The embodiments are intended to be illustrative in all respects, rather than restrictive, of the present invention. It is to be understood that various combinations and permutations of various parts and components of the schemes disclosed herein can be implemented by one skilled in the art without departing from the scope of the present invention. For example, although the figures show the barrier frame to be a closed ring, gaps can be made in the ring. All U.S. patents and U.S. patent publications cited herein are incorporated by reference herein in their entireties.

What is claimed is:

1. A device for administration of a pharmaceutical agent to an individual through a body surface, comprising:
   a. a reservoir having a first matrix comprising at least one pharmaceutical agent in the first matrix, the reservoir having a reservoir outer perimeter;
   b. a first backing layer attached to the reservoir and substantially impermeable to the pharmaceutical agent, the first backing layer having a first backing layer outer perimeter;
   c. a second matrix layer permeable to the pharmaceutical agent, the second matrix layer having a second matrix layer outer perimeter; and
   d. a barrier layer disposed between the reservoir and at least part of the second matrix layer, the barrier layer having a barrier layer outer perimeter that is smaller than the second matrix layer outer perimeter, the reservoir outer perimeter being smaller than the barrier layer outer perimeter, the barrier layer being of a material that is substantially impermeable to the pharmaceutical agent wherein the barrier layer has a window through which at least one of the second matrix layer and the first backing layer can extend to attach to the other layer;
   wherein at least part of the second matrix layer is disposed above the reservoir, as measured from the surface to which the device is applied.

2. The device of claim 1 wherein the second matrix layer is an adhesive, and wherein the reservoir outer perimeter and the first backing layer outer perimeter are the same size.

3. The device of claim 2 further comprising a second backing layer, wherein the second backing layer is attached to the second matrix layer and is positioned more distal from the reservoir, the second backing layer having a second backing layer outer perimeter, and wherein the first backing layer outer perimeter is smaller than the second backing layer outer perimeter.

4. The device of claim 1 wherein the second matrix layer is an adhesive that maintains the device on the body surface for at least two days, and wherein the second matrix layer is attached to the first backing layer.

5. The device of claim 1 wherein the first matrix further comprises an acrylate polymer in which the pharmaceutical agent is soluble.

6. The device of claim 1 further comprising a second backing layer,
   wherein the second backing layer is attached to the second matrix layer and is positioned more distal to the reservoir,
   and wherein the second matrix layer is an adhesive that maintains the device on the body surface for at least two days.

7. The device of claim 3 wherein the second matrix layer contains a second pharmaceutical agent.

8. The device of claim 1 wherein the device has an intended shelf life and the reservoir exhibits cold flow during the shelf life such that the reservoir outer perimeter enlarges during the shelf life but does not exceed the barrier layer outer perimeter.

9. The device of claim 3 further comprising a third backing layer and a third matrix layer, wherein the third backing layer is attached to the third matrix layer and is positioned more distal to the reservoir, the third matrix layer having a third matrix layer outer perimeter and the third backing layer having a third backing layer outer perimeter,
   wherein the third matrix layer outer perimeter is the same size as the third backing layer outer perimeter but larger than the barrier layer outer perimeter,
   and wherein the third matrix layer contains a second pharmaceutical agent and is disposed intermediate to the reservoir and the third backing layer.

10. The device of claim 3 further comprising a third matrix layer and a third backing layer, the third matrix layer having a third matrix layer outer perimeter and the third backing layer having a third backing layer outer perimeter,
    wherein the third matrix having a third matrix layer outer perimeter is the same size as the third backing layer outer perimeter but smaller than the window of the barrier layer,
    wherein the third matrix layer is disposed intermediate to the reservoir and the second matrix layer and can extend in the window to attach to the first backing layer,
    and wherein the third matrix layer contains a second pharmaceutical agent.

11. The device of claim 3 wherein the device is made by mechanized mass production.

12. A device for administration of a pharmaceutical agent to an individual at a therapeutically effective rate through a body surface, comprising:

a. a reservoir having a first matrix comprising at least one pharmaceutical agent in the first matrix, the reservoir having a reservoir outer perimeter;
b. a first backing layer attached to the reservoir and substantially impermeable to the pharmaceutical agent, the first backing layer having a first backing layer outer perimeter;
c. a second matrix layer permeable to the pharmaceutical agent, the second matrix layer having a second matrix layer outer perimeter;
d. a second backing layer attached to the second matrix layer, the second backing layer having a second backing layer outer perimeter; and
e. a barrier layer disposed intermediate to the reservoir and at least part of the second matrix layer, the barrier layer having a barrier layer outer perimeter, the barrier layer being a material that is substantially impermeable to the pharmaceutical agent, and the barrier layer having a window through which at least one of the second matrix layer and the first backing layer can extend to attach to the other;
wherein the second backing layer outer perimeter is the same size as the second matrix layer outer perimeter but larger than the barrier layer outer perimeter,
and wherein the first backing layer outer perimeter is the same size as the reservoir outer perimeter but smaller than the barrier layer outer perimeter.

* * * * *

UNITED STATES PATENT AND TRADEMARK OFFICE
CERTIFICATE OF CORRECTION

PATENT NO.         : 8,632,800 B2
APPLICATION NO.    : 11/433343
DATED              : January 21, 2014
INVENTOR(S)        : Jansen et al.

It is certified that error appears in the above-identified patent and that said Letters Patent is hereby corrected as shown below:

In the Specification

Column 2, Line 38 reads, "...tics (e.g., theological parameters), a system may change over..." which should read, "...tics (e.g., rheological parameters), a system may change over..."

Column 3, Line 31 reads, "...crossing over to anther matrix layer." which should read, "...crossing over to another matrix layer."

Column 3, Line 50 reads, "...(either that of a overlay or another reservoir matrix), the..." which should read, "...(either that of an overlay or another reservoir matrix), the..."

Column 4, Line 57 reads, "...an reservoir that incorporates pharmaceutical agent (or drug)..." which should read, "...a reservoir that incorporates pharmaceutical agent (or drug)..."

Column 5, Line 35 reads, "...a matrix layer can be a layer that contain a drug, an antagonist..." which should read, "...a matrix layer can be a layer that contains a drug, an antagonist..."

Column 10, Line 24 reads, "...to the skin is a acrylate adhesive having a glass transition..." which should read, "...to the skin is an acrylate adhesive having a glass transition..."

Column 12, Line 55 reads, "...subsequent operations, the laminate is further processes in..." which should read, "...subsequent operations, the laminate is further processed in..."

Column 16, Line 59 reads, "...construction showed in FIGS. 16 and 17. Multiple frames and..." which should read, "...construction shown in FIGS. 16 and 17. Multiple frames and..."

Column 17, Line 18 reads, "...Barrier frames (84) is die cut from a 1 mil (0.025 mm) thick..." which should read, "...Barrier frames (84) are die cut from a 1 mil (0.025 mm) thick..."

Signed and Sealed this
Seventh Day of October, 2014

Michelle K. Lee
*Deputy Director of the United States Patent and Trademark Office*